United States Patent
Min et al.

(10) Patent No.: US 10,589,100 B2
(45) Date of Patent: Mar. 17, 2020

(54) METHOD AND DEVICE FOR PACING LATENCY BASED MULTI-POINT PACING

(71) Applicant: PACESETTER, INC., Sylmar, CA (US)

(72) Inventors: Xiaoyi Min, Simi Valley, CA (US); Kyungmoo Ryu, Palmdale, CA (US); Stuart Rosenberg, Castaic, CA (US); David Muller, Sicklerville, NJ (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 15/702,479

(22) Filed: Sep. 12, 2017

(65) Prior Publication Data
US 2019/0076652 A1 Mar. 14, 2019

(51) Int. Cl.
*A61N 1/368* (2006.01)
*A61N 1/05* (2006.01)
*A61B 5/0452* (2006.01)
*A61B 5/00* (2006.01)
*A61B 5/07* (2006.01)

(52) U.S. Cl.
CPC .......... *A61N 1/3682* (2013.01); *A61B 5/0452* (2013.01); *A61B 5/076* (2013.01); *A61B 5/4836* (2013.01); *A61N 1/056* (2013.01); *A61N 1/36842* (2017.08); *A61N 1/36843* (2017.08)

(58) Field of Classification Search
CPC .. A61N 1/3682; A61N 1/056; A61N 1/36843; A61N 1/368
See application file for complete search history.

(56) References Cited

U.S. PATENT DOCUMENTS

| 7,778,706 B1 * | 8/2010 | Min ................... A61N 1/36542 607/9 |
| 8,442,634 B2 | 5/2013 | Min |
| 8,565,880 B2 | 10/2013 | Dong |

(Continued)

FOREIGN PATENT DOCUMENTS

WO    2017074999    5/2017

OTHER PUBLICATIONS

European Search Report dated Oct. 8, 2018; Application No. 18186494.3.

*Primary Examiner* — William J Levicky
(74) *Attorney, Agent, or Firm* — Dean D. Small; The Small Patent Law Group, LLC

(57) ABSTRACT

Methods and devices are is provided for controlling a pacing therapy utilizing left ventricular multi-point pacing (MPP). The method and device provide electrodes configured to be located proximate to an atrial (A) site, a right ventricular (RV) site and multiple left ventricular (LV) sites of the heart. The method and device utilizes one or more processors. The processors determine atrial-ventricular conduction delays (AVCD) between the A site and multiple corresponding LV sites and determines pacing latencies at the LV sites. The processors adjusts the AVCDs, based on the pacing latency at the corresponding LV sites, to form atrial-ventricular latency adjusted (ARPL) conduction delays for the corresponding LV sites, calculates interventricular pacing (VV) delays for combinations of the LV sites based on the corresponding ARPL conduction delays and manages pacing therapy, that utilizes left ventricular MPP, based on the VV delays for the corresponding LV sites.

18 Claims, 8 Drawing Sheets

(56) References Cited

U.S. PATENT DOCUMENTS

| | | |
|---|---|---|
| 2004/0147966 A1 | 7/2004 | Ding |
| 2004/0193223 A1 | 9/2004 | Kramer |
| 2005/0209649 A1 | 9/2005 | Ferek petric |
| 2006/0047320 A1 | 3/2006 | Ding |
| 2006/0235481 A1 | 10/2006 | Fogoros et al. |
| 2008/0269826 A1 | 10/2008 | Lian |
| 2010/0069987 A1 | 3/2010 | Min |
| 2010/0145405 A1 | 6/2010 | Min |
| 2010/0222834 A1 | 9/2010 | Sweeney |
| 2011/0098772 A1 | 4/2011 | Min |
| 2011/0137369 A1* | 6/2011 | Ryu ................ A61N 1/368 607/27 |
| 2012/0165892 A1 | 6/2012 | Min |

* cited by examiner

METHOD AND DEVICE FOR PACING LATENCY BASED MULTI-POINT PACING

BACKGROUND

Embodiments of the present disclosure generally relate to methods and devices for controlling a timing of multi-point pacing therapy based on pacing latency.

Clinical studies related to cardiac pacing have shown that a desired (e.g., optimal) atrio-ventricular pacing delay (e.g., AV delay or PV delay) and/or a desired (e.g., optimal) interventricular pacing delay (e.g., VV delay) can improve cardiac performance. However, achieving a desired delay depends on a variety of factors that may vary over time. Thus, what is "desired" may vary over time. Selection of a desired AV/PV pacing delay and/or VV pacing delay may occur at implantation and sometimes, may occur during a follow-up consultation. Once the AV/PV and VV pacing delays are set, the benefits may not be long lasting due to changes in various factors related to device and/or cardiac function. Various systems and methods are provided for, inter alia, allowing a pacemaker or IMD to determine and/or adjust AV/PV/VV pacing delays so as to help maintain the pacing delays at desired values. In particular, techniques were set forth for exploiting various interventricular conduction delays to determine AV/PV/VV pacing delays.

Other techniques have been set forth for determining AV/PV delays based on inter-atrial conduction delays and interventricular conduction delays. In particular, see U.S. Pat. No. 7,248,925, to Bruhns et al., entitled "System and Method for Determining Optimal Atrioventricular Delay based on Intrinsic Conduction Delays," which is fully incorporated by reference herein.

Certain types of patients (e.g., patients experiencing heart failure), who receive unipolar and bipolar cardiac resynchronization therapy (CRT) devices, may experience challenges such as phrenic nerve stimulation, high pacing thresholds and nonresponse to CRT therapy. Managing these challenges can result in longer implant times and surgical revisions. Today, new types of CRT devices are being utilized with a lead located proximate to the left ventricle (LV) that includes multiple electrodes distributed along the LV lead. For example, a quadripolar LV lead has been introduced that includes four distributed LV electrodes, such as to provide multi-point pacing (MPP) in a single coronary sinus branch.

While the availability of an MPP LV lead provides further improvement to CRT clinical outcomes, a desire remains to improve further timing and automatic programming guidance.

SUMMARY

In accordance with embodiments herein, a method is provided for controlling a pacing therapy utilizing left ventricular multi-point pacing (MPP). The method provides electrodes configured to be located proximate to an atrial (A) site, a right ventricular (RV) site and multiple left ventricular (LV) sites of the heart. The method utilizes one or more processors. The processors determine atrial-ventricular conduction delays (AVCD) between the A site and multiple corresponding LV sites and determines pacing latencies at the LV sites. The processors adjusts the AVCDs, based on the pacing latency at the corresponding LV sites, to form atrial-ventricular latency adjusted (ARPL) conduction delays for the corresponding LV sites, calculates interventricular pacing (VV) delays for combinations of the LV sites based on the corresponding ARPL conduction delays and manages pacing therapy, that utilizes left ventricular MPP, based on the VV delays for the corresponding LV sites.

Optionally, the calculating operation may calculate ΔARPL differences between the ARPL conduction delays for combinations of the LV sites, calculate site-to-site incremental ventricular (IVV) pacing delays for the corresponding combinations of the LV sites based on the ΔARPL differences and may calculate interventricular pacing (VV) delays for corresponding combinations of the LV sites based on a related subset of the IVV pacing delays. The IVV pacing delays may include an interventricular pacing delay between the RV site and a first LV site, and an intraventricular pacing delay between the first LV site and a second LV site.

Optionally, the method may compare the pacing latencies at the LV sites to one or more thresholds and may update a candidate LV site list based on the comparing operation. At least one of the LV sites may be removed from the candidate LV site list when the corresponding pacing latency is greater than the corresponding threshold. The method may compare the ΔARPL differences with one or more thresholds and updating an candidate LV site list based on the comparing operation. The candidate LV site list may maintain a list of candidate LV sites to deliver pacing therapy. At least one of the LV sites may be removed from the candidate LV site list when the ΔARPL difference is less than the corresponding threshold.

Optionally, when the ΔARPL difference between first and second LV sites falls below the corresponding threshold, the method may further comprise comparing first and second bordering ΔARPL differences associated with the first and second LV sites, respectively, and removing a one of the first and second LV sites from the candidate LV site list based on the comparing of the first and second bordering ΔARPL differences. The combinations of the LV sites may represent adjacent pairs of LV sites the managing operation may utilize a first VV delay to deliver pacing pulses to a first LV site and a second VV delay to deliver pacing pulses to a second LV site. The method may determine the atrial-ventricular conduction delay ($AR_{RV}$) between the A site and the RV site; and setting the AVCD based on a difference between the $AR_{RV}$ and the VV delay.

In accordance with embodiments herein, a system is provided for controlling a pacing therapy utilizing left ventricular multi-point pacing (MPP). The system comprises electrodes configured to be located proximate to an atrial (A) site, a right ventricular (RV) site and multiple left ventricular (LV) sites of the heart. The system further includes memory to store program instructions and one or more processors configured to implement the program instructions to perform. The system determines atrial-ventricular conduction delays (AVCD) between the A site and multiple corresponding LV sites and determines pacing latencies at the LV sites. The system adjusts the $AR_{LV}$ delays, based on the pacing latency at the corresponding LV sites, to form atrial-ventricular latency adjusted (ARPL) conduction delays for the corresponding LV sites. The system calculates interventricular pacing (VV) delays for combinations of the LV sites based on the corresponding ARPL conduction delays and manages a pacing therapy, that utilizes left ventricular MPP, based on the VV delays for the corresponding LV sites.

Optionally, the one or more processors may further be configured to perform the calculating by calculating ΔARPL differences between the ARPL conduction delays for combinations of the LV sites, calculating site-to-site incremental ventricular (IVV) pacing delays for the corresponding combinations of the LV sites based on the ΔARPL differences and calculating interventricular pacing (VV) delays for corresponding combinations of the LV sites based on a related subset of the IVV pacing delays. The one or more processors may be further configured to determine a correction term ε based an intrinsic inter-ventricular conduction delay (IVCD) between the RV and LV and may set an interventricular pacing delay VV delay based on the correction term ε.

Optionally, the IVV pacing delays may include an interventricular pacing delay between the RV site and a first LV site, and an intra-ventricular pacing delay between the first LV site and a second LV site. The IVV pacing delays may include at least first and second intra-ventricular pacing delays between corresponding combinations of the LV sites. The one or more processors may be further configured to compare the pacing latencies at the LV sites to one or more thresholds and update a candidate LV site list based on the comparing operation.

Optionally, the one or more processors may be further configured to remove at least one of the LV sites from the candidate LV site list when the corresponding pacing latency is greater than the corresponding threshold. The one or more processors may be further configured to compare the ΔARPL differences with one or more thresholds and update an candidate LV site list based on the comparing operation. The candidate LV site list may maintain a list of candidate LV sites to deliver pacing therapy. The one or more processors may be further configured to remove at least one of the LV sites from the candidate LV site list when the ΔARPL difference is less than the corresponding threshold.

DETAILED DESCRIPTION

Figure 1:
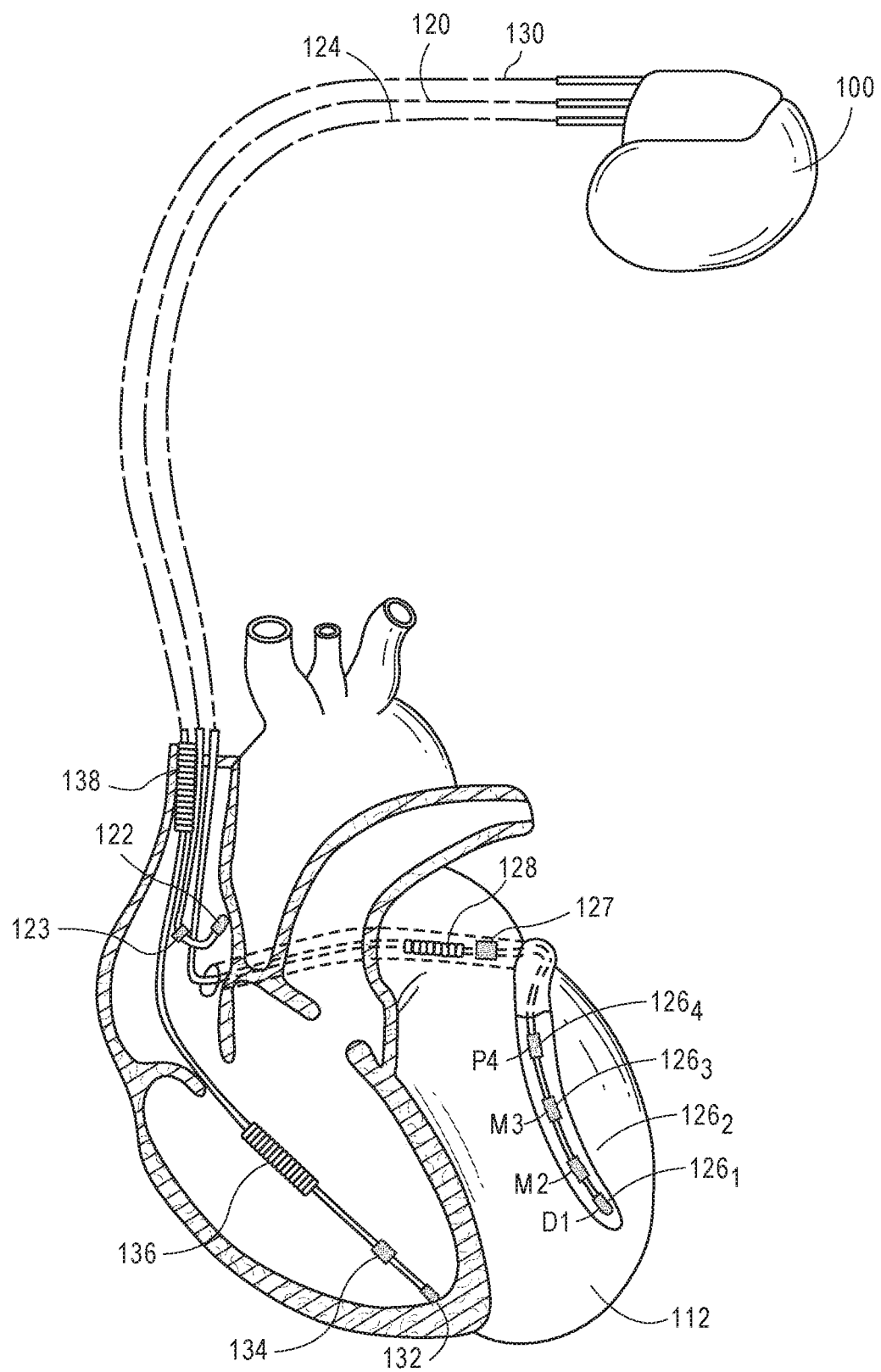
FIG. 1 illustrates an exemplary IMD formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The terms "atrial-ventricular conduction delay", "$AR_{LV}$", "$AR_{RV}$" and "AVCD" refer to a time interval experienced between an occurrence of an intrinsic or paced event in an atria and an occurrence of a related evoked response at a site of interest in a right ventricle (RV) or a left ventricle (LV). The term "AVCD" is used to refer to measurements between an atria and either of the RV or LV. When the AVCD is measured between an atria and the RV, the resulting atrial-ventricular conduction delay to the RV is also referred to as $AV_{RV}$ delay. When the AVCD is measured between an atria and the LV, the resulting atrial-ventricular conduction delay is also referred to as the $AV_{LV}$ delay.

The term "pacing latency" or "PL" refers to a time period or interval between i) delivery of a paced event at a pacing electrode and ii) an evoked compound action potential sensed at the same pacing electrode.

The term "ARPL difference" refers to a difference between $AV_{LV}$ for combinations of the LV sites, such as differences between the AVCD for adjacent pairs of LV sites. The ΔARPL difference represents an incremental conduction delay between a corresponding pair of LV sites that is estimated/determined based on the $AV_{LV}$ for the corresponding pair of LV sites.

The terms "site-to-site incremental ventricular pacing delay" or "IVV pacing delay" refer to an incremental delay utilized in connection with calculating delays for pacing therapy, where the incremental delay is between a combination of sites. For example, an IVV pacing delay may correspond to one RV site and one LV site, or an adjacent pair of LV sites. As a further example, when an LV lead includes four electrodes located at different points along the left ventricle, separate IVV pacing delays may be assigned to the proximal and Mid1 electrode pair, the Mid1 and Mid2 electrode pair, and the Mid2 and distal electrode pair.

The terms "interventricular pacing delay" or "VV delay" refer to a delay utilized by an IMD in connection with timing delivery of a paced event at an LV site following delivery of a paced event (or sensing of an intrinsic event) at an RV site. As explained herein, the VV delay for one or more LV sites is determined based on a combination of IVV pacing delays for corresponding RV and LV sites.

Embodiments may be implemented in connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$, also referred to as a proximal LV electrode, a $Mid_1$ LV electrode, a $Mid_2$ LV electrode and a distal LV electrode, respectively. For example, the LV electrodes $126_1$-$126_4$ may be provided on a quadripole lead for left atrial pacing therapy. Shocking therapy may utilize at least a left atrial coil electrode 128 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead.

Implantable Medical Device

Figure 2:
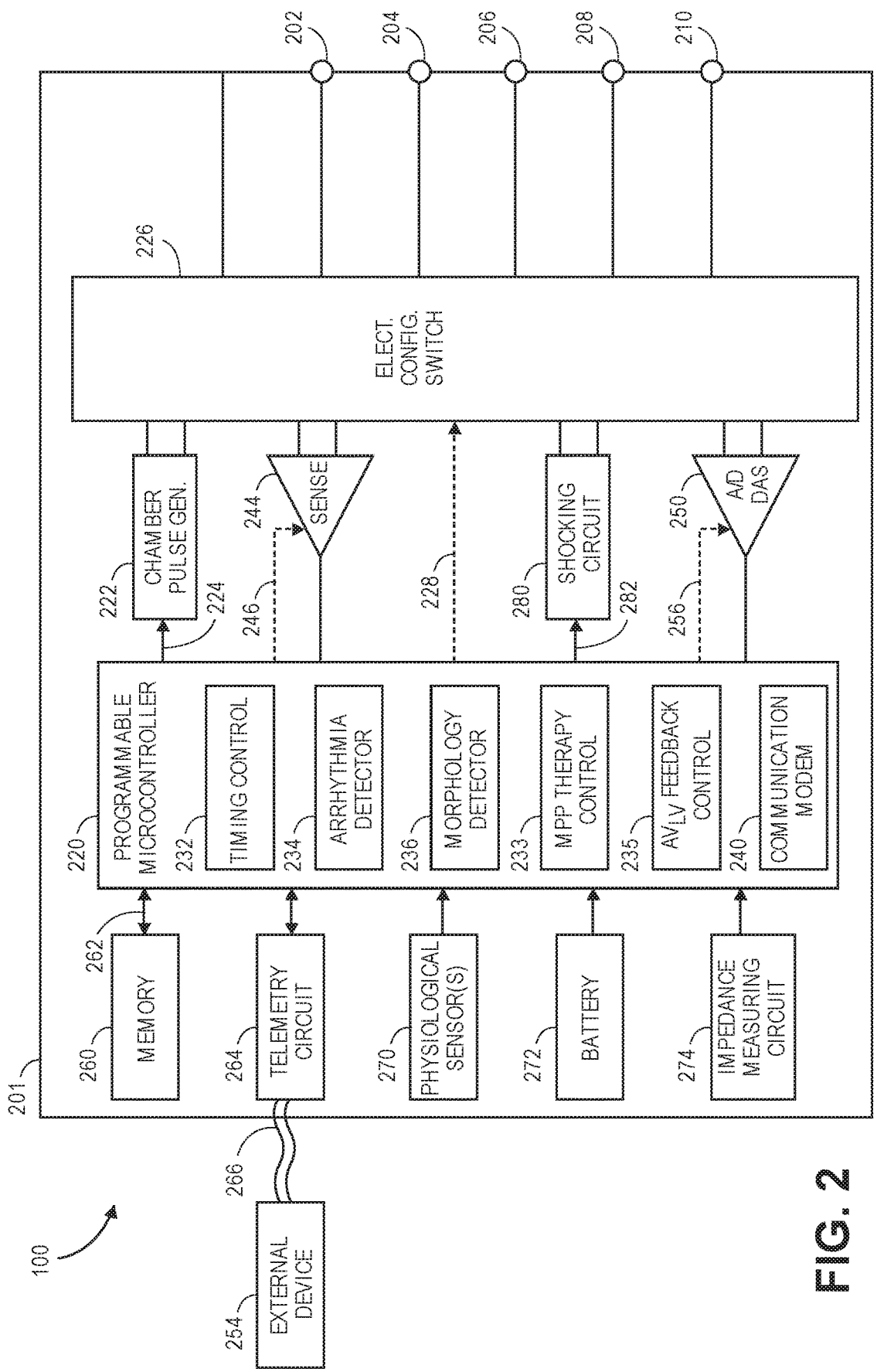
FIG. 2 shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components.

The IMD 100 has a housing 201 to hold the electronic/ computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

Microcontroller 220 is illustrated to include timing control circuitry 232 to control the timing of the stimulation pulses (e.g., pacing rate, atrio-ventricular (AV) delay, atrial interconduction (A-A) delay, or ventricular interconduction (V-V) delay, etc.). In connection with embodiments herein, the timing control circuitry 232 is used to manage LV atrial-ventricular ($AV_{LV}$) delays that are set as described herein. The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector 236 to review and analyze one or more features of the morphology of cardiac signals.

The microcontroller 220 includes MPP therapy control circuitry 233 to implement the processes described herein for controlling MPP pacing therapy adjusted for pacing latency and including/excluding certain LV sites. The MPP therapy control circuitry 233 determines atrial-ventricular conduction ($AR_{LV}$) delays between the A site and multiple corresponding LV sites. The MPP therapy control circuitry 233 determines pacing latencies at the LV sites. The MPP therapy control circuitry 233 adjusts the $AR_{LV}$ delays, based on the pacing latency at the corresponding LV sites, to form atrial-ventricular latency adjusted (ARPL) conduction delays for the corresponding LV sites. The MPP therapy control circuitry 233 calculates interventricular pacing (VV) delays for combinations of the LV sites based on the corresponding ARPL conduction delays. The MPP therapy control circuitry 233 manages a pacing therapy, that utilizes left ventricular MPP, based on the VV delays for the corresponding LV sites.

As explained in connection with FIGS. 3A and 3B, the MPP therapy control circuitry 233 performs the adjustment by calculating ΔARPL differences between the ARPL conduction delays for combinations of the LV sites, and calculating site-to-site incremental ventricular (IVV) pacing delays for the corresponding combinations of the LV sites based on the ΔARPL differences. The MPP therapy control circuitry 233 further calculates interventricular pacing (VV) delays for corresponding combinations of the LV sites based on a related subset of the IVV pacing delays.

The MPP therapy control circuit 233 is further configured to determine a correction term ε based an intrinsic interventricular conduction delay (IVCD) between the RV and LV; and set an interventricular pacing delay VV delay based on the correction term ε. The IVV pacing delays may include an interventricular pacing delay between the RV site and a first LV site, and an intra-ventricular pacing delay between the first LV site and a second LV site. The IVV pacing delays may include at least first and second intra-ventricular pacing delays between corresponding combinations of the LV sites. The MPP therapy control circuit 233 is further configured to compare the pacing latencies at the LV sites to one or more thresholds and update a candidate LV site list based on the comparing operation. The MPP therapy control circuit 233 is further configured to remove at least one of the LV sites from the candidate LV site list when the corresponding pacing latency is greater than the corresponding threshold. The MPP therapy control circuit 233 is further configured to compare the ΔARPL differences with one or more thresholds and update an candidate LV site list based on the comparing operation, the candidate LV site list maintaining a list of candidate LV sites to deliver pacing therapy. The MPP therapy control circuit 233 is further configured to remove at least one of the LV sites from the candidate LV site list when the ΔARPL difference is less than the corresponding threshold.

Figure 5:
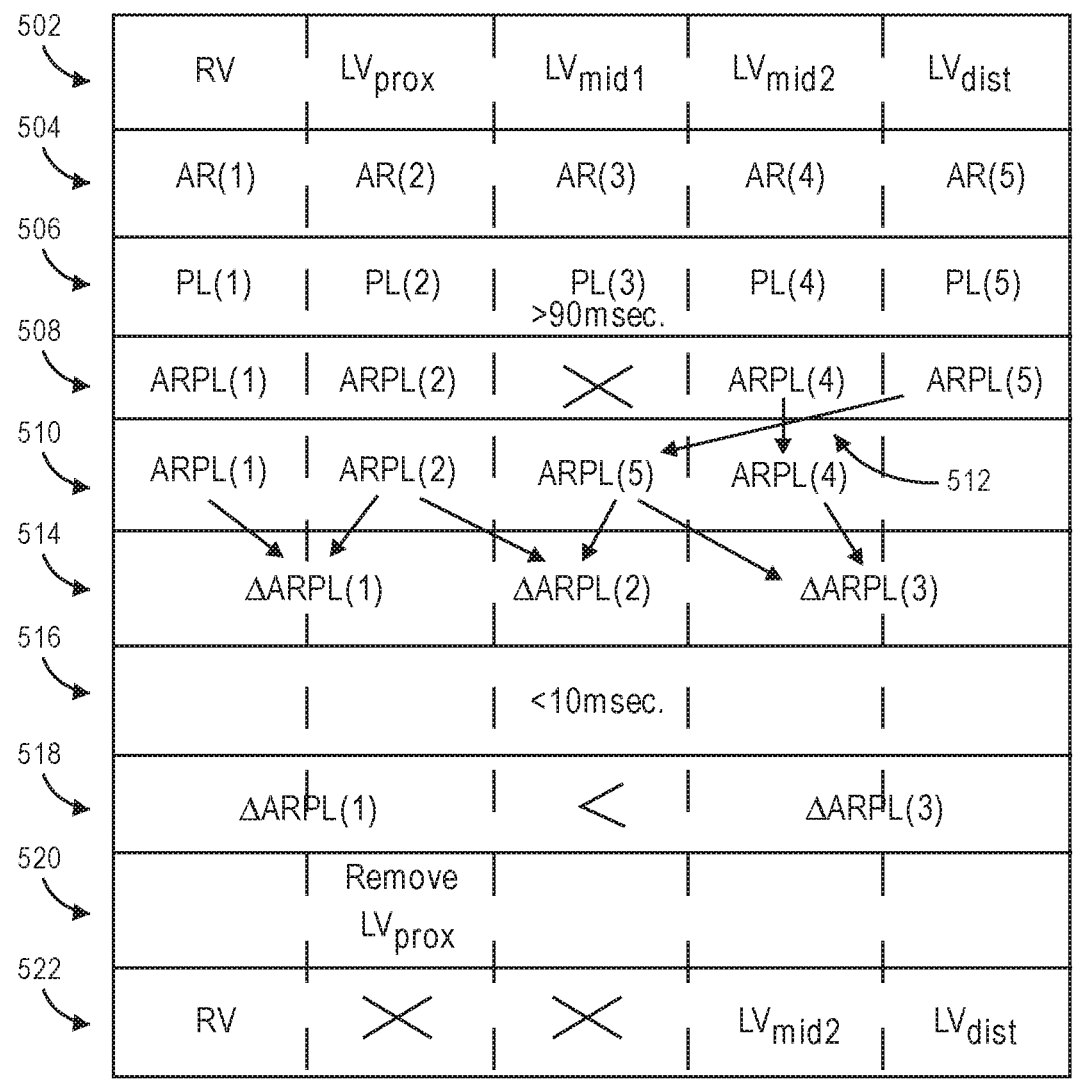
FIG. 5 illustrates a table to provide an example of one manner by which candidate LV pacing sites may be analyzed to identify a resultant LV site list in accordance with an embodiment herein.

The memory 260 is configured to store a candidate LV site list. The candidate LV site list maintains a list of candidate LV sites to deliver pacing therapy. For example, initially, the candidate LV site list includes proximal, $Mid_1$, $Mid_2$, and distal LV sites. As explained herein, the candidate site list is updated by removing one or more LV sites to obtain a resultant LV site list (stored in memory 260) that designates the LV sites to use during MPP therapy. The memory 260 also stores $AV_{LV}$ delays between A sites and multiple corresponding LV sites, stores pacing latencies at the LV sites, and adjustments to the $AR_{LV}$ delays, based on the pacing latency at the corresponding LV sites, to form atrial-ventricular latency adjusted (ARPL) conduction delays for the corresponding LV sites. The memory 260 stores VV delays for combinations of the LV sites and pacing therapies that utilizes left ventricular MPP, based on the VV delays for the corresponding LV sites. FIG. 5 illustrates an example of the type of information that may be stored in the memory 260.

Although not shown, the microcontroller 220 may further include other dedicated circuitry and/or firmware/software components that assist in monitoring various conditions of the patient's heart and managing pacing therapies. Optionally, an $AV_{LV}$ feedback control circuitry 235 may be provided to manage feedback to confirm the MPP pacing therapy. The $AV_{LV}$ feedback control circuitry 235 may use at least one of QRS related feedback, mechanical di-synchrony related feedback or stroke volume surrogate related feedback. For example, the $AV_{LV}$ feedback control circuitry 235 may analyze a paced QRS width in connection with multiple $AV_{LV}$ delays, and select one or more $AV_{LV}$ delays corresponding to the paced QRS width having a criteria of interest. Optionally, the $AV_{LV}$ feedback control circuitry 235 may analyze a contractility time delay in connection with multiple $AV_{LV}$ delays, and select one or more $AV_{LV}$ delays corresponding to the contractility time delay having a criteria of interest. Optionally, the $AV_{LV}$ feedback control circuitry 235 may analyze a stroke volume impedance in connection with multiple $AV_{LV}$ delays, and select one or more $AV_{LV}$ delay corresponding to the stroke volume impedance having a criteria of interest.

The IMD 100 is further equipped with a communication modern (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuitry 244 selectively coupled to one or more electrodes that perform sensing operations, through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the sensing circuitry 244 is connected to the microcontroller 220 which, in turn, triggers or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 244 is illustrated. Optionally, the IMD 100 may include multiple sensing circuit, similar to sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or in a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include magnet detection circuitry (not shown), coupled to the microcontroller 220, to detect when a magnet is placed over the unit. A magnet may be used by a clinician to perform various test functions of the unit 200 and/or to signal the microcontroller 220 that the external programmer 254 is in place to receive or transmit data to the microcontroller 220 through the telemetry circuits 264.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 200, the physiologic sensor(s) 270 may be external to the unit 200, yet still be implanted within or carried by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 200 employs lithium/silver vanadium oxide batteries.

The IMD 100 further includes an impedance measuring circuit 274 that is enabled by the microcontroller 220 via a control signal 282. As explained herein, the impedance measuring circuit 274 may be utilized in a feedback loop to collect cardiogenic impedance signals along one or more impedance vectors while delivering an MPP pacing therapy having an $AV_{LV}$ delay defined in accordance with embodiments herein. For example, the cardiogenic impedance signals may be collected as described in U.S. Pat. No. 8,923,965 "Systems and Methods for Optimizing AV/VV Pacing Delays Using Combined IEGM/Impedance-Based Techniques for use with Implantable Medical Devices"; and U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are incorporated herein by reference in their entirety.

The impedance measuring circuit 274 may also be used for: performing lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 211 to 40 joules), as controlled by the microcontroller 220. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Pacing Therapy

Figure 3A:
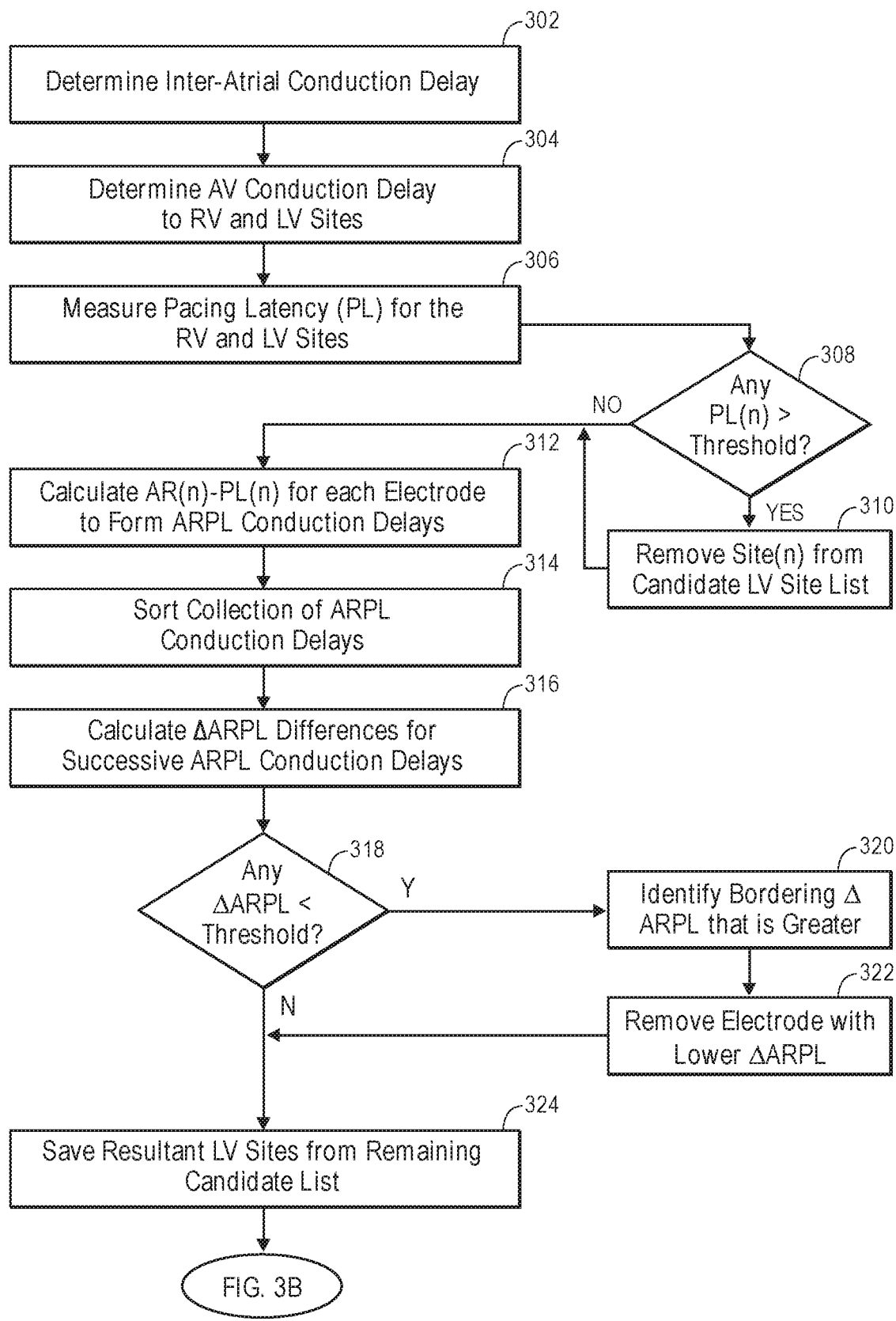
FIG. 3A illustrates a process for controlling a cardiac pacing therapy for an IMD in accordance with embodiments herein.
Figure 3B:
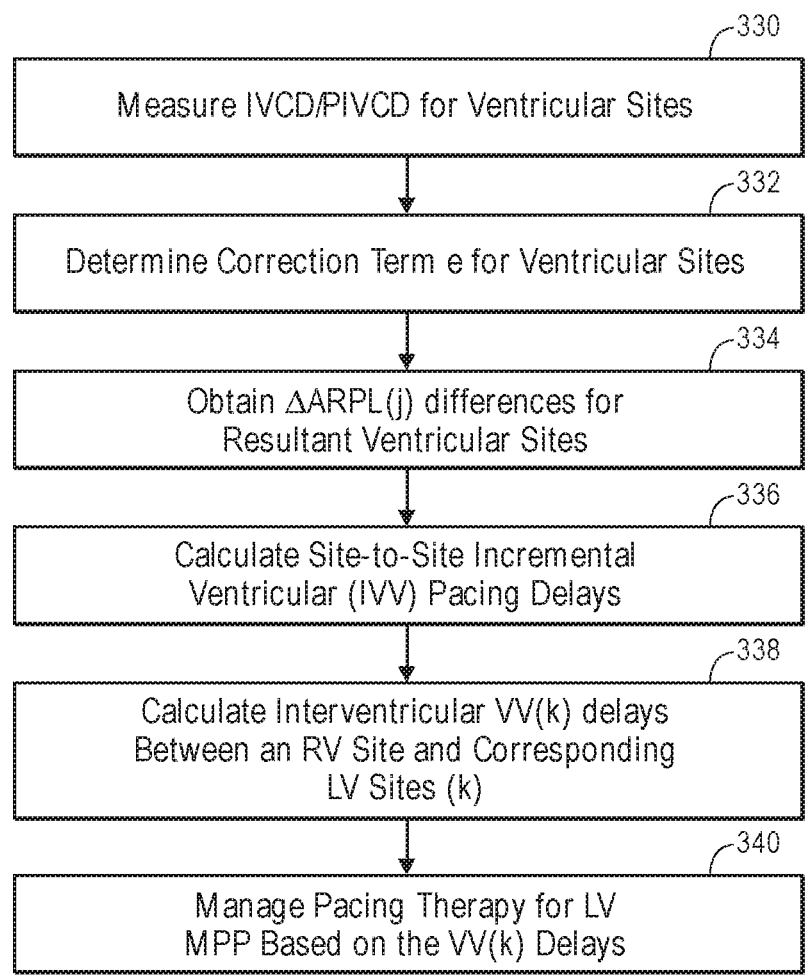
FIG. 3B illustrates a process for controlling a cardiac pacing therapy for an IMD in accordance with embodiments herein.

FIGS. 3A and 3B illustrate a process for controlling a cardiac pacing therapy for an IMD in accordance with embodiments herein. All or a portion of the operations of FIGS. 3A and 3B may be performed by one or more processors of an IMD, an external device, a server operating on a medical network and the like. Optionally, the operations of FIGS. 3A and 3B may be implemented in combination with the systems and methods described in U.S. Pat. No. 8,442,634; 8,923,965 and/or U.S. Patent Application Publication 2014/0039333.

The operations of FIG. 3A may be performed with respect to a candidate LV site list. At 302, the one or more processors determine an inter-atrial conduction (A-A) delay (also referred to herein as IACT delay). The IACT delay may be measured between atrial sensing sites in the left atrium and right atrium. Optionally, the inter-atrial conduction A-A delay may be estimated based on the duration of atrial events, i.e. the duration of P-waves or atrial evoked responses. Additional information regarding options for the determination and utilization of inter-atrial conduction delays is set forth in U.S. Pat. No. 7,248,925, cited above. Herein, inter-atrial delays refer to delays measured between two points on or within one or both of the atria. In the exemplary embodiments described herein, one point is on or within the left atrium and the other is on or within the right atrium. However, other embodiments may involve measurements taken between two points on or within one atrial chamber. Accordingly, these inter-atrial delays may alternatively be referred to as intra-atrial delays.

At 304, the one or more processors determine atrial-ventricular conduction delays (AVCD) between an atrial (A) site and multiple available ventricular (RV and/or LV) sites (n), where n corresponds to an $n^{th}$ electrode/site. The conduction delay may be referred to as an AR(n) delay when based on a paced atrial event and conduction delay may be referred to as a PR(n) delay when based on a sensed atrial event (AR and PR delays are collectively ALCD). For example, a tip RV electrode may represent one RV site. An LV lead may include four electrodes that each represent a separate LV site, such as proximal, $Mid_1$, $Mid_2$, and distal locations along the LV lead. More RV electrode sites may be utilized and/or more or fewer LV electrode sites may be utilized. The AR(n) delays may be measured based on an intrinsic event detected in an atrium and/or PR(n) delays may be measured based on a paced event that is delivered in the atrium. By way of example, one or more timers may be activated when a paced or sensed event is identified in the atrium. The timer(s) continue until a corresponding intrinsic event is detected at a corresponding ventricular electrode site.

Figure 4A:
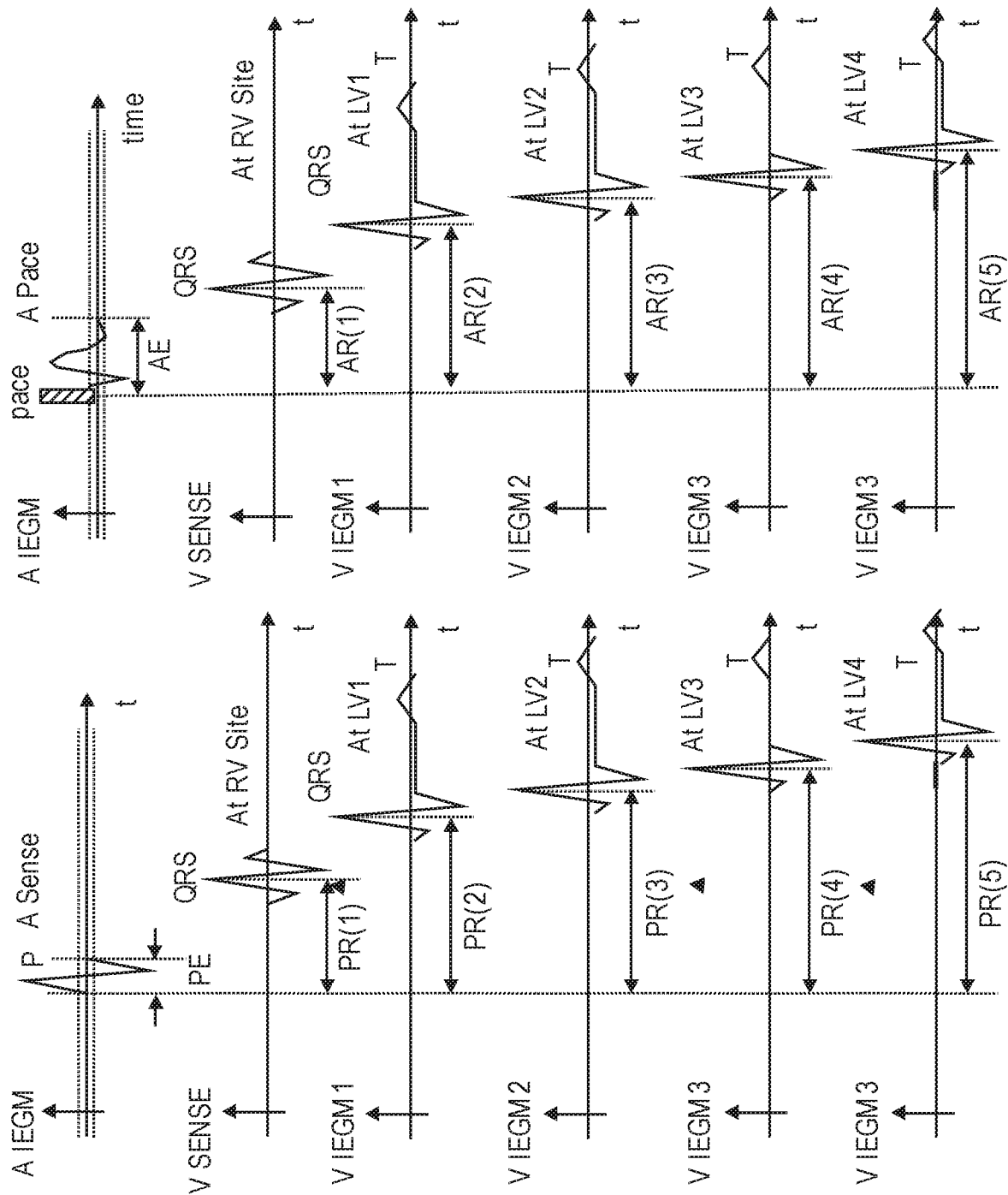
FIG. 4A illustrates example signals sensed at atrial and ventricular sites that may be utilized for determining the inter-atrial conduction (A-A) delay, the atrial-ventricular conduction AR(n) delays and the atrial-ventricular conduction PR(n) delays in accordance with embodiments herein.

FIG. 4A illustrates example signals sensed at atrial and ventricular sites that may be utilized for determining the inter-atrial conduction (A-A) delay, the atrial-ventricular conduction AR(n) delays and the atrial-ventricular conduction PR(n) delays in accordance with embodiments herein. The one or more processors measure the IACT delay. The duration of the P-wave is referred to herein as PE. The duration of the atrial evoked response is referred to herein as AE. In FIG. 4A, a P-wave (A-Sense) is illustrated to have a duration PE and an atrial paced event (A_Pace) illustrated to have a duration AE. FIG. 4 further illustrates five ventricular sensing channels (corresponding to five electrodes), that include one RV electrode (channel) and 4 LV electrodes (channels). The RV channel is labeled V_SENSE, while the LV channels are labeled V_IEGM1 to V_IEGM4 which correspond to the proximal, $Mid_1$, $Mid_2$ and distal electrodes. The ventricular sensing channels V_IEGM1 to V_IEGM4 illustrate example evoked responses that are sensed in response to the intrinsic P-wave "A_Sense". The RV channel senses an evoked response (labeled QRS) that follows the intrinsic P-wave "A_Sense" by an interval PR(1). Thereafter, the LV channels V_IEGM1 to V_IEGM4 (e.g., proximal, $Mid_1$, $Mid_2$ and distal electrodes) sense corresponding evoked responses after intervals PR(2), PR(3), PR(4) and PR(5), respectively, at LV electrodes LV1-LV4 (e.g., corresponding to LV electrodes $126_1$ to $126_4$ in FIG. 1).

The ventricular sensing channels V_IEGM1-V_IEGM4 also illustrate example evoked responses that are sensed in response to the paced event "A_Pace". The RV channel senses an evoked response (labeled QRS) that follows the paced event A_Pace by an interval AR(1). Thereafter, the LV channels V_IEGM1-V_IEGM4 (e.g., proximal, $Mid_1$, $Mid_2$ and distal electrodes) sense corresponding evoked responses after intervals AR(2), AR(3), AR(4) and AR(5), respectively, at LV electrodes LV1-LV4.

With respect to 304 in FIG. 3A, in connection with intrinsic atrial events, the processors measure the PR(n) delays as the corresponding one of the intervals PR(2), PR(3), PR(4) and PR (5).

In connection with paced atrial events, the processors measure the AR(n) delays as the corresponding one of the intervals AR(2), AR(3), AR(4) and AR(5). Returning to FIG. 3A, at 304, the one or more processors measure and save the PR(n) delays and/or the AR(n) delays (collectively AVCD).

At 306, the one or more processors determine a pacing latency (PL(n)) at all or a portion of the available sites for which AR(n) or PR(n) delays were determined. For example, with reference to FIG. 1, a pacing latency PL(1) may be measured at the RV site 132 (corresponding to the RV tip electrode) and pacing latencies PL(2)-PL(5) may be measured at four LV sites $126_1$-$126_4$. The pacing latency PL(n) may be measured by measuring a latency interval between a paced event delivered at a corresponding RV/LV site and an evoked compound action potential (ECAP) sensed at the same RV/LV site. In the present example, the measurement at 306 is shown to be performed during the operations of FIG. 3A. However, optionally, the measurement at 306 may be performed at any time independent of, separate from and/or in parallel with, the other operations of FIG. 3A. For example, the pacing latency may be obtained through follow-up pacing test, or extracted during an "auto-capture" operation during a device download process. As a further example, the pacing latency may be determined during delivery of a pacing therapy, such as following any RV and/or LV paced event. The pacing latency may be recorded for future use during the process of FIG. 3A.

At 308, the one or more processors analyze the pacing latencies PL(n) relative to one or more latency thresholds. The processors determine whether the pacing latencies PL(n) exceed a common or corresponding latency thresholds. A site that exhibits unduly long pacing latency may be indicative of unhealthy tissue at the corresponding site. For example, a site, having a pacing latency that is greater than a corresponding threshold (e.g., 90 msec.), may indicate that the corresponding electrode is located within an ischemic or infarcted zone of tissue. Ischemic and infarcted zones may also exhibit unduly long mechanical contraction delays. Accordingly, it may be desirable to remove a pacing site from the candidate LV site list when the pacing site is within an ischemic or infarcted zone of tissue. The latency threshold(s) may be programmed by a clinician, or set automatically by the IMD based on feedback obtained during operation. By way of example, a latency threshold may be 80 msec, 90 msec, 100 msec, etc. Optionally, the latency threshold may be dynamically adjusted based on the patient's physiologic behavior, such as the resting heart rate, current heart rate, activity level, and the like. At 308, the processors identify whether one or more sites have a pacing latency that exceeds the corresponding latency threshold. When one or more sites exhibit a pacing latency that exceeds a threshold, flow moves to 310. When none of the sites have pacing latencies that exceed the corresponding threshold, flow moves to 312.

At 310, the one or more processors remove, from the candidate LV site list, the sites (n) that exhibit pacing latencies greater than the corresponding latency threshold. As explained herein, the methods and systems maintain and update the candidate LV site list to form a resultant LV site list. The resultant LV site list includes LV sites that may be used MPP therapy. For example, the candidate LV site list may initially include each of the LV electrodes provided on the LV lead. As explained herein, various criteria may be applied to determine whether a particular LV site represents a good candidate for delivering pacing pulses. Certain LV sites may not represent good candidates, such as explained above when an LV site is within an ischemic or infarcted zone. As another example, an LV site may not represent a good pacing candidate when a different between the ARPL conduction delays of the present LV site and an adjacent LV site is extremely small. When two LV sites exhibit a very small difference in ARPL conduction delays, the two LV sites effectively operate as a single site during pacing, and thus it may be desirable to choose only one of the two LV sites to deliver a pacing therapy.

At 312, the one or more processors perform an adjustment in connection with the LV sites on the candidate LV site list. For example, the processors adjust the AR or PR delays (also referred to as $AR_{LV}(n)$ delays and/or $PR_{LV}(n)$ delays), based on the pacing latency at the corresponding LV sites, to form atrial-ventricular latency adjusted (ARPL(n)) conduction delays for corresponding LV sites. The ARPL(n) conduction delay for any given pacing site/electrode (n) may be calculated in various manners, such as based on a difference between the AR(n) delay and the PL(n) (e.g., ARPL(n)=AR(n)−PL(n) for electrodes n=1, 2, 3, . . . ) or (e.g., ARPL(n)= PR(n)−PL(n) for electrodes n=1, 2, 3, . . . ). Additionally or alternatively, the AR(n) delays may be calculated based on another mathematical combination of the AR(n) delay and PL(n), other than a difference. Additionally or alternatively, weighting factors may be added to the AR(n) delay and/or PL(n). The processors may store the ARPL(n) conduction delays in, or in connection with, the candidate LV sites. Optionally, the ARPL(n) conduction delays may be stored as a separate table, list or in other formats.

At 314, the one or more processors sort the collection of ARPL(n) conduction delays in ascending or descending order. Optionally, the collection of ARPL(n) conduction delays may be ordered in other manners.

At 316, the one or more processors calculate an ΔARPL difference for successive electrode pairs in the ARPL collection. For example, a first ΔARPL difference is calculated between the RV electrode and a proximal LV electrode (e.g., ARPL(1)−ARPL(2)), a second ΔARPL difference is calculated between the proximal and $Mid_1$ LV electrodes (e.g., ARPL(2)−ARPL(3)), a third ΔARPL difference is calculated between the $Mid_1$ and $Mid_2$ electrodes (e.g., ARPL(3)− ARPL(4)), a fourth ΔARPL difference is calculated between the $Mid_2$ and distal electrodes (e.g., ARPL(4)−ARPL(5)).

At 318, the one or more processors determine whether any of the ΔARPL differences exceed a corresponding threshold. A common threshold may be applied for all ΔARPL differences. Optionally, different thresholds may be applied in connection with different ΔARPL differences. When one or more ΔARPL differences fall below the threshold, flow moves to 320. Otherwise, flow moves to 324.

At 320, the one or more processors analyze bordering ΔARPL differences identified at 318. For example, the processors compare first and second bordering ΔARPL differences associated with the first and second LV sites, respectively. The ΔARPL differences correspond to differences between temporally adjacent ARPL conduction delays after the ARPL conduction delays are sorted and reordered in ascending or descending order. Accordingly, the first ΔARPL difference may be between ARPL conduction delays associated with first and second LV sites that are physically adjacent LV sites. Optionally, the first ΔARPL difference may be between ARPL conduction delays associated with first and second LV sites that are physically separated LV sites, but exhibit temporally adjacent conduction delays. For example, at 318, with reference to FIG. 1, a select ΔARPL difference may correspond to the $Mid_1$ and $Mid_2$ LV sites and be determined at 318 to have a value below a corresponding threshold (e.g., 10 msec.). When the ARPL conduction delays remain in the same order as the physical position of the LV sites, then the boarding first and second ΔARPL differences would be for 1) the proximal and $Mid_1$ electrode pair and 2) the $Mid_2$ and distal electrode pair. Alternatively, the ARPL conduction delays may not correspond to the physical position of the LV sites. For example, select ΔARPL difference may correspond to the $Mid_1$ and distal LV sites and be determined at 318 to have a value below a corresponding threshold (e.g., 10 msec.). The boarding first and second ΔARPL differences may be for 1) the proximal and $Mid_1$ electrode pair and 2) the $Mid_2$ and distal electrode pair. At 320, the processors determine which of the bordering ΔARPL differences is greater.

At 322, the processors remove, from the candidate LV site list, the shared electrode that is associated with the lower bordering ΔARPL difference. The processors retain, on the candidate LV site list, the shared electrode associated with the larger bordering ΔΔARPL difference. For example, in connection with the operations at 320-322, the processors compare first and second bordering ΔΔARPL differences associated with the first and second LV sites, respectively. The processors remove a one of the first and second LV sites from the candidate LV site list based on the comparing of the first and second bordering ΔΔARPL differences.

At 324, the one or more processors designate and save the sites that remain on the candidate LV site list, as the resultant LV site list. Thereafter, flow moves to FIG. 3B.

FIG. 5 illustrates a table to provide an example of one manner by which candidate LV pacing sites may be analyzed to identify a resultant LV site list in accordance with an embodiment herein. The row 502 represents an initial list of candidate sites that include an RV site and multiple candidate LV sites, namely Proximal, $Mid_1$, $Mid_2$ and Distal LV sites. At row 504, an atrial ventricular conduction AR (1)–AR (5) delay is determined in connection with the RV site and the four LV sites. At 506, pacing latencies are determined in connection with the RV and LV sites. Also at 506, the pacing latency associated with the $Mid_1$ LV site is determined to be greater than a threshold of 90 ms. Thus, the $Mid_1$ LV site is removed from the candidate LV site list (as noted by the "X"). At 508, the remaining AV conduction delays are adjusted for pacing latency to form the ARPL (1)–ARPL (2), ARPL (4) and ARPL (5) conduction delays.

At 510, the ARPL conduction delays are re-ordered in ascending order. In the example of FIG. 5, the ARPL conduction delay associated with the distal LV electrode is larger than the conduction delay associated with the $Mid_2$ LV electrode and thus the order is switched as denoted at 512.

At 514, ΔARPL differences, ΔARPL(1), ΔARPL(2) and ΔARPL (3) are calculated between successive ARPL conduction delays based on the order sorted at 510. In the present example, the ΔARPL(2) difference represents a difference between the ARPL conduction delays for the proximal LV electrode and the distal LV electrode, while the ΔARPL(3) difference represents a difference between the ARPL conduction delays for the distal LV electrode and the $Mid_2$ LV electrode.

At 516, the ΔARPL differences are compared with one or more thresholds. In the present example, the ΔARPL(2) difference is less than the corresponding threshold of 10 msec. In response thereto, at 518, a comparison is performed between the bordering ΔΔARPL differences associated with the LV sites forming the ΔARPL(2) difference. The comparison at 518 is between bordering ΔΔARPL(1) and ΔARPL (3) differences. In the present example, the ΔΔARPL(3) difference is greater than the ΔΔARPL(1) difference, and thus, at 520, the proximal LV electrode associated with the ΔΔARPL(1) difference is removed from the candidate LV site list. At 522, the remaining RV site, $Mid_2$ LV site and distal LV site form the resultant LV site list that is used in FIG. 3B.

FIG. 3B illustrates a continuation of the process of FIG. 3A. At 330, one or more processors measure an intrinsic inter-ventricular conduction delay (IVCD(m,n)) and/or paced-based interventricular conduction delay (PIVCD(m, n)) between the RV and each of the LV sites, where m represent an electrode site where an intrinsic or paced event occurred and n represents an electrode site where a corresponding sensed event is detected. For example, a PIVCD (1,3) may correspond a PIVCD between an RV electrode that delivers a paced event and a $Mid_1$ LV electrode that senses a corresponding evoked response. As another example, an IVCD(3,5) may correspond an IVCD between the $Mid_1$ LV electrode that delivers a paced event and a distal LV electrode that senses a corresponding evoked response. The interventricular conduction delay IVCD may be measured in either direction or in both directions based on intrinsic events sensed in the RV and LV. Optionally, the paced-based interventricular conduction delay PIVCD may be measured in either direction or both directions. Optionally, the intrinsic interventricular conduction delays may be based on sensed events in both the RV and LV.

Figure 4B:
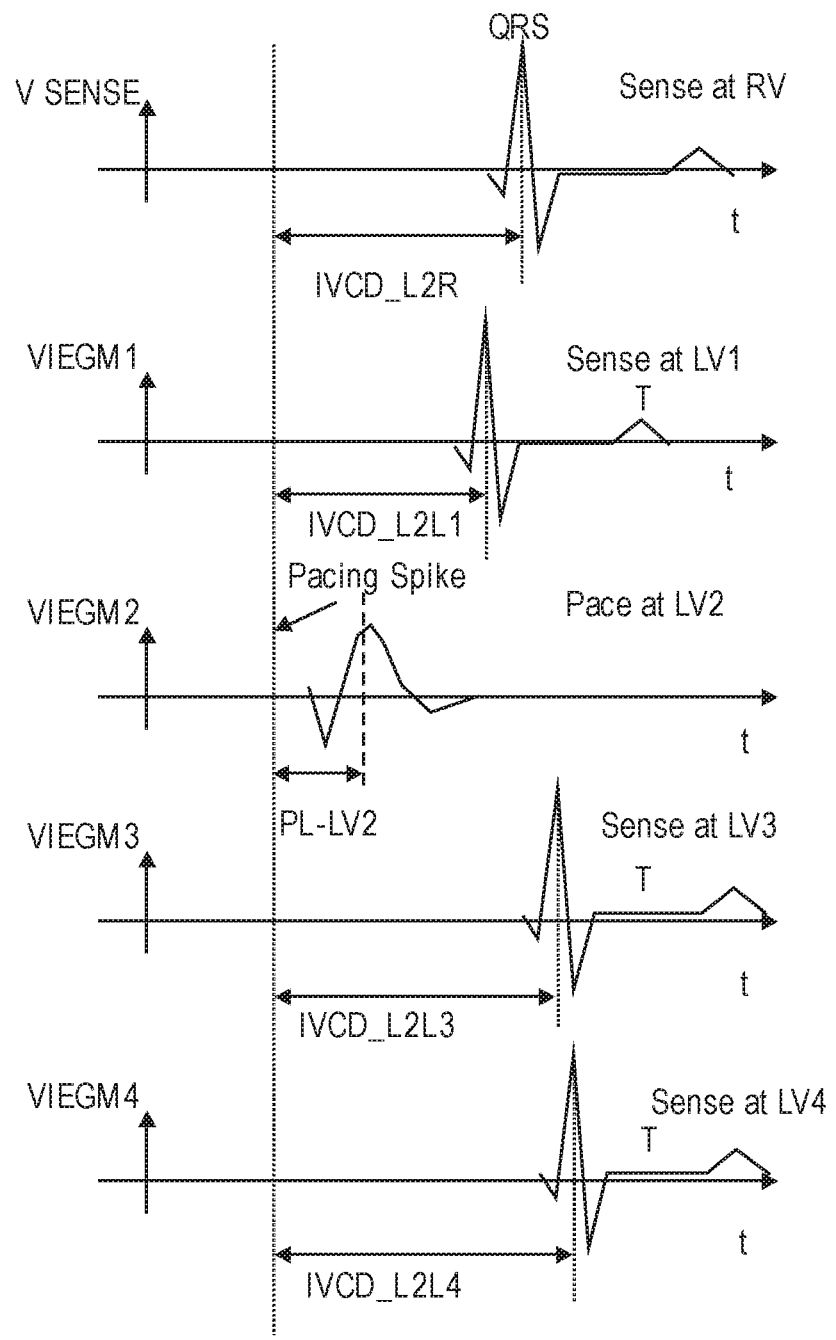
FIG. 4B illustrates example timing diagram of signals sensed at ventricular sites and utilized for measuring the IVCD(m,n) between RV and LV sites in accordance embodiments herein.

FIG. 4B illustrates example timing diagram of signals sensed at ventricular sites and utilized for measuring the IVCD(m,n) between RV and LV sites. The RV channel is labeled V_SENSE, while the LV channels are labeled V_IEGM1 to V_IEGM4 which correspond to the proximal, $Mid_1$, $Mid_2$ and distal electrodes. In the present example, the LV2 (Mid1) electrode delivers a paced event at the point denoted "pacing spike". Thereafter, the RV channel V_SENSE senses a QRS complex after a time period IVCD_L2R following the paced event at the LV2 electrode. The LV channel V_IEGM1 senses a ventricular event after the time period IVCD_L2L1 following a paced event at the LV2 (Mid1) electrode. The LV (Mid2) channel V_IEGM3 senses a ventricular event after the time period IVCD_L2L3 following the paced event. The LV (distal) channel V_IEGM4 senses a ventricular event after the time period IVCD_L2L4 following the paced event. A pacing latency PL-LV2 is measured at the LV (Mid1) channel V_IEGM2. The measurements illustrated in FIG. 4B represent one example of the measurements obtained at 330 in FIG. 3B.

At 332, the one or more processors determine a correction term ε(j) based on the intrinsic interventricular conduction delay IVCD or paced-based interventricular delay PIVCD for an electrode combination (j). Different correction terms ε are calculated for different electrode combinations. For example, the correction term ε(1) correspond to the electrode combination between the RV tip electrode and the proximal LV electrode. Accordingly, the correction term ε(1) may be set to equal the difference between the $PIVCD_{RL}(1)$ and $PIVCD_{LR}(1)$ (e.g., $\varepsilon(1)=PIVCD_{RL}(1)-PIVCD_{LR}(1)$) for the RV tip electrode and the proximal LV electrode. Optionally, the correction term ε may be based on a weighted difference between the $PIVCD_{RL}$ and $IVCD_{LR}$.

At 334-338, the one or more processors calculate interventricular pacing (VV) delays for one or more combinations of the RV and LV sites on the resultant LV site list. As explained herein, the VV delays are calculated based on the corresponding ARPL conduction delays. More particularly, at 334, the one or more processors obtain the ΔARPL(j) differences from memory (calculated at 316 in FIG. 3A) for the ventricular site combinations (j) on the resultant LV site list.

At 336, the one or more processors calculate site-to-site incremental ventricular (IVV) pacing delays for the corresponding combinations (j) of the LV sites based on the ΔARPL differences (ΔARPL(j)). For example, the processors may set the IVV(j) pacing delay for corresponding LV site combination (j) based on a combination of a weighting factor and the ΔARPL (j) difference for the corresponding LV site combination (j). For example, the following equation may be utilized to set the IVV pacing delay (j): IVV(j)= α*ΔARPL(j), where α is a non-zero natural number and j corresponds to the LV site combination.

Optionally, the IVV(j) pacing delays may be calculated utilizing the correction term ε determined above at 332. For example, the processors may set the IVV(j) pacing delay for corresponding LV site combination (j) based on a combination of a weighting factor multiplied by a sum of the correction term ε and the corresponding ΔARPL(j) difference. For example, the following equation may be utilized to set the IVV(j) pacing delays: IVV(j)=α*(ΔARPL(j)+ε(j)), where α is a non-zero natural number and j corresponds to a LV site combination.

At 338, the one or more processors calculate interventricular pacing (VV(k)) delays between an RV site and corresponding LV sites (k). The VV(k) delay for a given LV site is based on a subset of the IVV(j) pacing delays that extend between the RV site and the corresponding LV site (k). For example, the VV(1) delay may correspond to the inter-ventricular pacing delay between the RV tip electrode and the proximal LV electrode. Accordingly, the VV (1) delay would be set to equal the site-to-site incremental ventricular (IVV(1)) pacing delay between the RV tip electrode and the proximal LV electrode. As another example, the VV(2) delay between the RV tip electrode and the Mid$_2$ LV electrode is set to correspond to a sum of the incremental site-to-site ventricular pacing delays between 1) the RV tip and proximal LV electrodes, 2) the proximal LV and Mid$_1$ electrodes, and 3) the Mid$_1$ and Mid$_2$ electrodes. The processors calculate the VV(k) delays for each of the LV sites (k) on the resultant LV site list, and save the VV(k) delays in memory in connection with a pacing therapy. Optionally, the one or more processors may set the VV(k) delays based on weighted combinations of the IVV delays.

At 340, the one or more processors manage a pacing therapy that utilizes left ventricular MPP, based on the VV(k) delays for the corresponding LV sites (k). For example, the pacing therapy may call for multipoint pacing to be delivered to the proximal LV electrode, Mid$_2$ electrode and distal LV electrode. The VV(k) delays may define intervals between successive pulses that are delivered at the proximal LV electrode, Mid$_2$ electrode and distal LV electrode. For example, the managing operation may utilize a first VV delay to deliver pacing pulses to a first LV site (e.g., proximal LV electrode) and a second VV delay to delivery pacing pulses to a second LV site (e.g., Mid$_2$ LV electrode).

As one example, when a paced or sensed atrial event occurs, the IMD sets a timer corresponding to the LV atrial-ventricular pacing delay $AV_{LV}$. If the timer corresponding to the LV atrial-ventricular pacing delay $AV_{LV}$ times out before an intrinsic ventricular event is sensed in the LV, the IMD delivers MPP pacing stimulation to at least two LV sites with an interval between the pulses delivered at the LV sites separated by the IVV delay for the corresponding LV site. In accordance with the process of FIGS. 3A and 3B, the pacing therapy does not pace certain LV sites, such as sites located within a schematic or infarcted zones and/or exhibit a very small conduction delay relative to an adjacent LV site. It is recognized that the pacing therapy determined in accordance with the operations of FIGS. 3A and 3B may perform right ventricular and/or atrial pacing.

External Device

Figure 6:
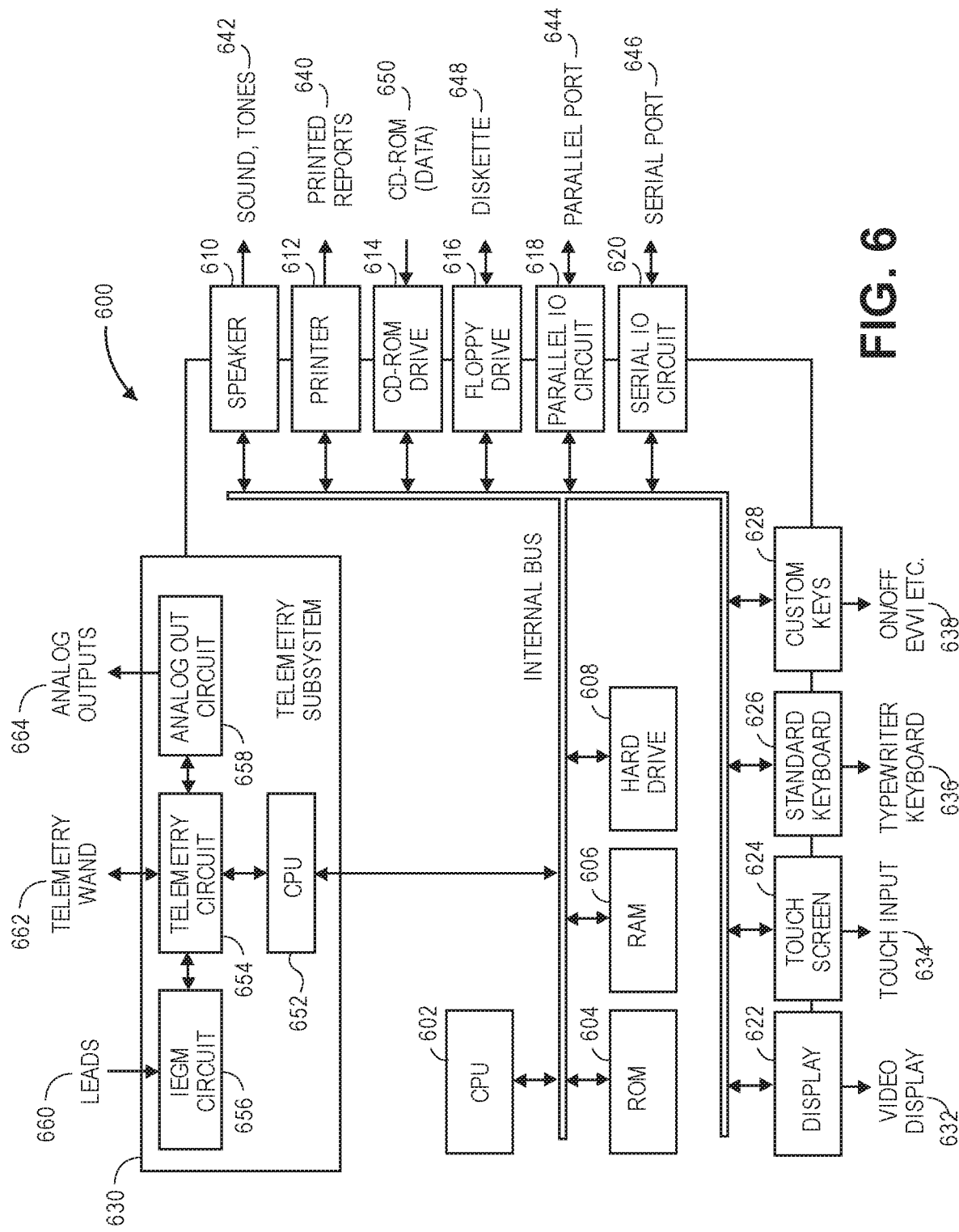
FIG. 6 illustrates a functional block diagram of the external device that is operated in accordance with the processes described herein and to interface with implantable medical devices as described herein.

FIG. 6 illustrates a functional block diagram of the external device 600 that is operated in accordance with the processes described herein and to interface with implantable medical devices as described herein. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a micro-controller, or equivalent control circuitry, designed specifically to control interfacing with the external device 600 and with the IMD 100. The CPU 602 performs the COI measurement process discussed above. The CPU 602 may include RAM or ROM memory, logic and timing circuitry, state machine circuitry, and I/O circuitry to interface with the IMD 100. The CPU 602 may implement some or all of the operations of the MPP therapy control circuitry 233 (FIG. 2) and/or the $AV_{LV}$ feedback control circuitry 235 (FIG. 2). The CPU 602 may implement some or all of the operations of the methods described herein, such as in connection with FIGS. 3A, 3B, 4 and 5.

The display 622 (e.g., may be connected to the video display 632). The touch screen 624 may display graphic information relating to the IMD 100. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads to receive and process IEGM cardiac signals as discussed above. Optionally, the IEGM cardiac signals sensed by the leads may be collected by the IMD 100 and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for controlling a pacing therapy utilizing left ventricular multi-point pacing (MPP), the system comprising:
    electrodes configured to be located proximate to an atrial (A) site, a right ventricular (RV) site and multiple left ventricular (LV) sites of the heart;
    memory to store program instructions;
    one or more processors configured to implement the program instructions to perform:
    determining atrial-ventricular conduction delays (AVCD) between the A site and multiple corresponding LV sites;
    determining pacing latencies at the LV sites;
    adjusting the AVCDs, based on the pacing latency at the corresponding LV sites, to form atrial-ventricular latency adjusted (ARPL) conduction delays for the corresponding LV sites;
    calculating interventricular pacing (VV) delays for combinations of the LV sites based on the corresponding ARPL conduction delays; and
    managing a pacing therapy, that utilizes left ventricular MPP, based on the VV delays for the corresponding LV sites;
    wherein the one or more processors are further configured to:
    calculate an intrinsic inter-ventricular conduction delay (IVCD) between the RV and LV; and
    determine a correction term ε based the IVCD and set the VV delay based on the correction term ε.

2. The system of claim 1, wherein the one or more processors are further configured to perform the calculating by:
    calculating ΔARPL differences between the ARPL conduction delays for combinations of the LV sites;
    calculating site-to-site incremental ventricular (IVV) pacing delays for the corresponding combinations of the LV sites based on the ΔARPL differences; and
    calculating interventricular pacing (VV) delays for corresponding combinations of the LV sites based on a related subset of the IVV pacing delays.

3. The system of claim 1, wherein the VV pacing delays include an interventricular pacing delay between the RV site and a first LV site, and an intra-ventricular pacing delay between the first LV site and a second LV site.

4. The system of claim 1, wherein the VV pacing delays include at least first and second intra-ventricular pacing delays between corresponding combinations of the LV sites.

5. The system of claim 1, wherein the one or more processors are further configured to calculate ΔARPL differences between the ARPL conduction delays for combinations of the LV sites, compare the ΔARPL differences with one or more thresholds and update an candidate LV site list based on the comparing operation, the candidate LV site list maintaining a list of candidate LV sites to deliver pacing therapy.

6. The system of claim 5, wherein the one or more processors are further configured to remove at least one of the LV sites from the candidate LV site list when the ΔARPL difference is less than the corresponding threshold.

7. A system for controlling a pacing therapy utilizing left ventricular multi-point pacing (MPP), the system comprising:
    electrodes configured to be located proximate to an atrial (A) site, a right ventricular (RV) site and multiple left ventricular (LV) sites of the heart;
    memory to store program instructions;
    one or more processors configured to implement the program instructions to perform:
    determining atrial-ventricular conduction delays (AVCD) between the A site and multiple corresponding LV sites;
    determining pacing latencies at the LV sites;
    adjusting the AVCDs, based on the pacing latency at the corresponding LV sites, to form atrial-ventricular latency adjusted (ARPL) conduction delays for the corresponding LV sites;
    calculating interventricular pacing (VV) delays for combinations of the LV sites based on the corresponding ARPL conduction delays; and
    managing a pacing therapy, that utilizes left ventricular MPP, based on the VV delays for the corresponding LV sites;
    wherein the one or more processors are further configured to compare the pacing latencies at the LV sites to one or more thresholds and update a candidate LV site list based on the comparing operation.

8. The system of claim 7, wherein the one or more processors are further configured to remove at least one of the LV sites from the candidate LV site list when the corresponding pacing latency is greater than the corresponding threshold.

9. A method for controlling a pacing therapy utilizing left ventricular multi-point pacing (MPP), the method comprising:
    providing electrodes configured to be located proximate to an atrial (A) site, a right ventricular (RV) site and multiple left ventricular (LV) sites of the heart;
    utilizing one or more processors to perform:
    determining atrial-ventricular conduction delays (AVCD) between the A site and multiple corresponding LV sites;
    determining pacing latencies at the LV sites, wherein the determining the AVCD further comprises determining an atrial-ventricular conduction delay ($AR_{RV}$) between the A site and the RV site;
    adjusting the AVCDs, based on the pacing latency at the corresponding LV sites, to form atrial-ventricular latency adjusted (ARPL) conduction delays for the corresponding LV sites;
    calculating interventricular pacing (VV) delays for combinations of the LV sites based on the corresponding ARPL conduction delays; and
    managing a pacing therapy, that utilizes left ventricular MPP, based on the VV delays for the corresponding LV sites.

10. The method of claim 9, wherein the calculating operation further comprises:
    calculating ΔARPL differences between the ARPL conduction delays for combinations of the LV sites;
    calculating site-to-site incremental ventricular (IVV) pacing delays for the corresponding combinations of the LV sites based on the ΔARPL differences; and
    calculating the VV delays for corresponding combinations of the LV sites based on a related subset of the IVV pacing delays.

11. The method of claim 9, where the VV delays include an interventricular pacing delay between the RV site and a first LV site, and an intra-ventricular pacing delay between the first LV site and a second LV site.

12. A method for controlling a pacing therapy utilizing left ventricular multi-point pacing (MPP), the method comprising:
providing electrodes configured to be located proximate to an atrial (A) site, a right ventricular (RV) site and multiple left ventricular (LV) sites of the heart;
utilizing one or more processors to perform:
determining atrial-ventricular conduction delays (AVCD) between the A site and multiple corresponding LV sites;
determining pacing latencies at the LV sites;
comparing the pacing latencies at the LV sites to one or more thresholds and updating a candidate LV site list based on the comparing operation;
adjusting the AVCDs, based on the pacing latency at the corresponding LV sites from the candidate LV site list, to form atrial-ventricular latency adjusted (ARPL) conduction delays for the corresponding LV sites;
calculating interventricular pacing (VV) delays for combinations of the LV sites based on the corresponding ARPL conduction delays; and
managing a pacing therapy, that utilizes left ventricular MPP, based on the VV delays for the corresponding LV sites.

13. The method of claim 12, wherein at least one of the LV sites is removed from the candidate LV site list when the corresponding pacing latency is greater than the corresponding threshold.

14. A method for controlling a pacing therapy utilizing left ventricular multi-point pacing (MPP), the method comprising:
providing electrodes configured to be located proximate to an atrial (A) site, a right ventricular (RV) site and multiple left ventricular (LV) sites of the heart;
utilizing one or more processors to perform:
determining atrial-ventricular conduction delays (AVCD) between the A site and multiple corresponding LV sites;
determining pacing latencies at the LV sites, wherein the determining the AVCD further comprises determining an atrial-ventricular conduction delay ($AR_{RV}$) between the A site and the RV site;
adjusting the AVCDs, based on the pacing latency at the corresponding LV sites, to form atrial-ventricular latency adjusted (ARPL) conduction delays for the corresponding LV sites;
calculating interventricular pacing (VV) delays for combinations of the LV sites based on the corresponding ARPL conduction delays; and
managing a pacing therapy, that utilizes left ventricular MPP, based on the VV delays for the corresponding LV sites, further comprising calculating $\Delta$ARPL differences between the ARPL conduction delays for combinations of the LV sites, comparing the $\Delta$ARPL differences with one or more thresholds and updating a candidate LV site list based on the comparing operation, the candidate LV site list maintaining a list of candidate LV sites to deliver pacing therapy.

15. The method of claim 14, wherein at least one of the LV sites is removed from the candidate LV site list when the $\Delta$ARPL difference is less than the corresponding threshold.

16. The method of claim 14, wherein, when the $\Delta$ARPL difference between first and second LV sites falls below the corresponding threshold, the method further comprising comparing first and second bordering $\Delta$ARPL differences associated with the first and second LV sites, respectively, and removing a one of the first and second LV sites from the candidate LV site list based on the comparing of the first and second bordering $\Delta$ARPL differences.

17. The method of claim 14, wherein the combinations of the LV sites represent adjacent pairs of LV sites.

18. A method for controlling a pacing therapy utilizing left ventricular multi-point pacing (MPP), the method comprising:
providing electrodes configured to be located proximate to an atrial (A) site, a right ventricular (RV) site and multiple left ventricular (LV) sites of the heart;
utilizing one or more processors to perform:
determining atrial-ventricular conduction delays (AVCD) between the A site and multiple corresponding LV sites;
determining pacing latencies at the LV sites;
adjusting the AVCDs, based on the pacing latency at the corresponding LV sites, to form atrial-ventricular latency adjusted (ARPL) conduction delays for the corresponding LV sites;
calculating interventricular pacing (VV) delays for combinations of the LV sites based on the corresponding ARPL conduction delays; and
managing a pacing therapy, that utilizes left ventricular MPP, based on the VV delays for the corresponding LV sites, the managing the pacing therapy utilizes a first VV delay to deliver pacing pulses to a first LV site and a second VV delay to deliver pacing pulses to a second LV site.

* * * * *